United States Patent [19]

Yang et al.

[11] Patent Number: 5,470,708
[45] Date of Patent: Nov. 28, 1995

[54] PARTICLE-MEDIATED TRANSFORMATION OF MAMMALIAN UNATTACHED CELLS

[76] Inventors: Ning-Sun Yang, 7802 Ox Trail Way, Verona, Wis. 53593; William F. Swain, 4922 Marathon Dr., Madison, Wis. 53705; Joseph K. Burkholder, 917 Midland St., Madison, Wis. 53715; Deborah L. Fuller, 6701 Park Edge Dr. Apt. D, Madison, Wis. 53719

[21] Appl. No.: 61,430

[22] Filed: Apr. 2, 1993

Related U.S. Application Data

[63] Continuation of Ser. No. 777,768, Oct. 15, 1991, abandoned.
[51] Int. Cl.$^6$ .............................. C12Q 1/68; C12N 15/90; C12N 5/16; C12N 5/22
[52] U.S. Cl. ........................ 435/6; 435/172.3; 435/240.2
[58] Field of Search ............................. 435/172.3, 240.1, 435/240.2, 240.5

[56] References Cited

U.S. PATENT DOCUMENTS

| | | | |
|---|---|---|---|
| 4,945,050 | 7/1990 | Sanford et al. | 435/172.1 |
| 5,015,580 | 5/1991 | Christon et al. | 435/172.3 |

FOREIGN PATENT DOCUMENTS 9100359  1/1991  WIPO .

OTHER PUBLICATIONS

Yang et al., *PNAS*, vol. 87, 1990, pp. 9568–9572.
Friedmann, T., "Progress Toward Human Gene Therapy," 244 *Science* 1275–1281 (1989).
Johnston, S. A., "Biolistic Transformation: Microbes To Mice," 34 *Nature* 776–777 (Aug. 1990).
Johnston, S. A., "In–Situ Introduction of Genes Into Tissues of the Living Mouse," Symposium on Particle Bombardment–Mediated Transformation of Plant and Animal Systems, Sponsored by Agracetus, Inc., Mar. 14–15, 1991.
Sanford, et al., "Delivery of Substances Into Cells and Tissues Using a Particle–Bombardment Process," 5 *Particulate Science and Technology* 27–37 (1987).
Sanford, J. C. "Recent Advances in Biolistic Technology," Symposium on Particle Bombardment–Mediated Transformation of Plant and Animal Systems, Sponsored by Agracetus, Inc., Mar. 14–15, 1991.
Sanford, J. C., "The Biolistic Process," 6 *TIBTECH* 299–302.
Yang, N. S., et al., "In Vivo and In Vitro Gene Transfer to Mammalian Somatic Cells by Particle Bombardment," Symposium on Particle Bombardment–Mediated Transformation of Plant and Animal Systems, Sponsored by Agracetus, Inc., March 14–15, 1991.
Zelenin, A. V., et al., "Genetic Transformation of Mouse Cultures Cells with Help of High–Velocity Mechanical DNA Injection", 244 FEBS Letters 65–67 (1989).
Benner, R., et al., "Antibody Formation in Bone Marrow," *In Immunological Methods* vol. 2, 248–250 (1981).
Human Growth Hormone Transient Gene Expression Assay System, *Nicholas Institute Diagnostics*.
MacGregor, et al., "histochemical Staining of Clonal Mammalian Cell Lines Expressing *E. coli*, Beta–glactosidase Indicates Heterogenous Expression of the Bacterial Gene," *Somatic Cell and Molecular Genetics* 253–265 (1987).
Quesenberry, P. J., "Hemopoietic Stem Cells, Progenitor Cells, and Growth Factors," *In Hematology* (1990).
*Selected Methods in Cellular Immunology*, 11, 22, 153, 205–208.
Wood, K. V., "Firefly Luciferase: A New Tool for Molecular Biologists," *Promega Notes* (Dec. 1990).
Miller, A. D., "Progress Toward Human Gene Therapy," 76 *Blood* 271–278 (1990).

*Primary Examiner*—Mindy B. Fleisher
*Assistant Examiner*—James Ketter

[57] ABSTRACT

A method of genetically transforming mammalian unattached cells is disclosed. The method begins by preparing copies of a nucleic acid construct and coating these copies onto biologically inert carrier particles. Mammalian unattached cells are isolated in a liquid suspension. The cell suspension is placed on a target surface, wherein the liquid is spread to a thin film on the target surface. In an alternative embodiment of the present invention, the liquid is spread onto a porous surface. The cells are bombarded with the construct-coated particles in such a fashion that some particles lodge in the interior of at least some of the cells. The existence and expression of the construct within the cell is verified.

12 Claims, 5 Drawing Sheets

PARTICLE-MEDIATED TRANSFORMATION OF MAMMALIAN UNATTACHED CELLS

This application is a continuation of application Ser. No. 07/777,768, filed Oct. 15, 1991, now abandoned.

FIELD OF THE INVENTION

The present invention relates to genetic transformation. In particular, the present invention relates to the insertion of foreign genetic material into mammalian hematopoietic and unattached cells.

BACKGROUND OF THE INVENTION

Mammalian blood cells are an attractive target for manipulation by genetic engineering. Many blood diseases are caused by defects in single genes, and these diseases could be treated through gene therapy by insertion of a single correct gene copy in appropriate cells. Examples of single gene defects are hemophilias, such as Factor IX deficiency and Factor VIII deficiency, and immuno-deficiencies, such as adenosine deaminase (ADA) deficiency. Manipulation of blood cells by the addition of a normal or corrective gene copy would provide a therapeutic strategy for treatment of these diseases. Blood cells are one of the ideal candidates for delivery of peptides or proteins systemically since they can secrete these products into the blood circulation. Genetic manipulation of blood cells in non-human animals may also be useful by providing experimental animal models for development of clinical protocols.

Lymphocytes have previously been the subject of genetic manipulation. Lymphocytes arise from the lymphoid system and comprise 20% of all leucocytes (white blood cells). During exposure to an antigen, specific lymphocytes are stimulated by the antigen. Stimulated lymphocytes may proliferate and produce antibodies to the antigen or may become part of a cellular immune response. The two major types of lymphocytes are T cells, which become helper or killer cells and are responsible for cellular immune response, and B cells, which produce antibodies.

In one prior example of genetic manipulation of lymphocytes, tumor infiltrating lymphocytes (TIL) have been isolated from melanoma tumors, infected with a retrovirus vector, and returned to patients. Rosenberg, et al., *N. Eng. J. Med.* 323: 570–578 (1990). The TILS were infected with the retrovirus simply to mark them so that their fate in the patient could be monitored. The study determined that the infused TILS persisted in the patient and produced no adverse effect. Recently, genetically transformed T and B cells have been proposed as a treatment for ADA deficiency. The T and B cells from ADA deficient patients would be infected with a retrovirus vector encoding an ADA gene, and these infected cells returned to the patient. Canto, et al., *Proc. Natl. Acad. Sci. USA* 83:6563–6567 (1986).

Bone marrow cells are another attractive target for genetic manipulation. Hematopoietic stem cells found in the bone marrow produce all the cells present in blood— lymphocytes, erythrocytes, platelets, granulocytes— macrophages and monocytes. Mitotic division of the stem cells produces two daughter cells, which either return to the stem cell pool or differentiate into a specific type of blood cell. Differentiation of stem cells involves consecutive cell differentiation and ends with the creation of various defined blood cell populations which live for up to a few months and then die. The hematopoietic system is an attractive target for gene transfer for several reasons. First, well-developed procedures exist for bone marrow transplantation. Second, hematopoietic cells develop into many different kinds of cells, and there are many genetic diseases that affect these blood cells.

Gene transfer into cells at different stages in the hematopoietic system will have different results. Transformed differentiated cells will express the gene transiently in a certain type of cell for a limited time— until the cell dies. Transformation of a stem cell can result in a continued stable expression of the gene, in all of the cells derived from that stem cell, for the life of the animal.

Several research groups have demonstrated gene transfer into hematopoietic stem cells of mice by procedures different than those of the present invention. A. D. Miller, *Blood* 76[2]: 271–278 (1990), describes a typical stem cell experiment. Donor animals were first treated with 5-fluorouracil to kill differentiated blood cells. This treatment was intended to induce the mitotic division of stem cells. Retrovirus vectors, which are effective for transformation only in dividing cells, were then exposed to the cells. The putatively transformed bone marrow was then injected into recipient animals. Recently, several groups have shown long-term expression of both the human beta-globin and the ADA gene in mice using the retrovirus procedure.

Miller (above, at 273) details some of the current problems in bone marrow genetic transformation. One particular problem is that "much of the repopulating ability of marrow is lost during the infection procedure." Miller points out that in applications where donors are limited, such as in humans, such losses may be a considerable practical obstacle to gene therapy.

What is needed in the art of gene transfer is an effective method of transforming unattached cells such as blood and hematopoietic cells. Previously, the vast majority of efforts directed at transformation of unattached cells have used retrovirus transformation vectors or electroporation. The apparatus used for the transformation technique of the present invention is based on a quite different method of transporting the foreign DNA into the genome of the target cells. As disclosed by Klein et al., *Nature*, 327: 70–73 (1987), an instrument for the acceleration of very small particles of metal, coated with DNA, is effective in causing transient expression in plant cells in vivo. The transforming DNA is coated onto very small particles which are shot as ballistic projectiles into the tissues to be transformed. While the apparatus described by Klein, et al. has been demonstrated to have utility in transforming plant cells in culture, this particular apparatus has the disadvantage that the force of particle impact is not readily adjustable. Thus, it is a difficult apparatus to use for transformation of different cells and organisms, because a wide range of kinetic energies of particle propulsion are not available. Yang, et al. (*Proc. Natl. Acad. Sci.* 87: 9568–9572 (December, 1990)) disclose a method of transforming solid tissue mammalian somatic cells in situ via particle bombardment. Yang, et al. employed a particle acceleration device with an adjustable voltage and transformed cell cultures and liver, skin and muscle tissues. A similar device is illustrated as effective in germ line transformation of plants in U.S. Pat. No. 5,015,580.

SUMMARY OF THE INVENTION

The present invention is a method of transforming unattached mammalian cells via particle bombardment. Cells are first isolated, suspended in liquid, and placed on a target surface. The amount of moisture on the target surface must be controlled, either by spreading the cell suspension into a thin film or by placing the cell suspension onto a porous surface. Particles are coated with copies of a nucleic acid construct, and the coated particles are accelerated into the supported unattached cells. The treated cells are then assayed for the presence or expression of the nucleic acid.

It is an object of the present invention to create transformed unattached cells.

It is another object of the present invention to create transformed lymphocytes capable of infusion or transplantation.

It is another object of the present invention to create transformed bone marrow cells capable of infusion.

An advantage of the present invention is that unattached cells are transformed easily and quickly. Because the method of the present invention is flexible and adaptable, the method is applicable to a wide variety of cells.

Another advantage of the present invention is that unattached cells are transformed in such a manner that they are still viable and proliferative.

Another advantage of the present invention is that the nucleic acid construct is delivered to the target cell by purely physical means.

Other objects, advantages and features will become apparent from the following specification, drawings and claims.

DETAILED DESCRIPTION OF THE INVENTION

The present invention is directed toward the transformation of unattached mammalian cells. By "unattached cells," it is meant cells that function independently in mammalian bodies and are not inherently structurally connected to other cells or a cellular matrix. Cells found in blood, such as lymphocytes and erythrocytes, and blood cell progenitors, such as bone marrow cells, are unattached cells as the term is used herein. Unattached cells useful in the present invention may be maintained as long-term primary cultures or as cell lines in culture. Cells may be isolated from these cultures and used in the method of the present invention. Unattached cells may also be directly isolated from a mammalian body.

By "transformation," we mean incorporation of a nucleic acid construct into a cell. The incorporation may be permanent or transient. The term "transformation" is used here only in the sense of genetic transformation through the insertion of a foreign nucleic acid construct and is not intended to describe the process of onset of malignancy in a cell which is also sometimes referred to as a transformation.

In brief, the method of the present invention involves first preparing copies of a nucleic acid construct and coating these construct copies onto biologically inert carrier particles. Mammalian unattached cells are isolated, suspended in liquid medium, and placed on a target surface. It is essential to the success of the present invention that the amount of moisture on the target surface is controlled. In one embodiment of the present invention, this is achieved by placing the liquid cell suspension on a porous surface. In another embodiment, the liquid cell suspension is spread out in a thin layer. These cells are "bombarded" with the construct-coated particles. The bombardment consists of physically accelerating the construct-coated particles into the cells on the target surface with an appropriate amount of force so that the particles lodge in the interior of at least some of the cells. As a final step, the expression of the construct or the existence of the construct in the cells is verified.

The invention is directed toward the introduction of exogenous, often chimeric, nucleic acid constructs into unattached cells. Such exogenous nucleic acid constructs consist of DNA or RNA from another organism, whether of the same or a different species. By the term "nucleic acid construct" we mean to include populations of RNA or DNA, as well as isolated and manipulated fragments.

The exogenous DNA construct would normally include a coding sequence for a transcription product or a protein of interest together with flanking regulatory sequences effective to cause the expression of the protein or the transcription product in the transformed cells of an organism. Examples of flanking regulatory sequences are a promoter sequence sufficient to initiate transcription and a terminator sequence sufficient to terminate the gene product whether by termination of transcription or translation. Suitable transcriptional or translational enhancers can be included in the exogenous gene construct to further assist the efficiency of the overall transformation process and expression of the encoded protein.

Gene products other than proteins may be expressed by the inserted nucleic acid construct. For example, the inserted construct could express a negative-strand RNA effective either to suppress the expression of a native gene or to inhibit a disease pathology. The construct could be RNA, as an alternative to DNA, if only transient expression of a gene product is desired.

Figure 1:
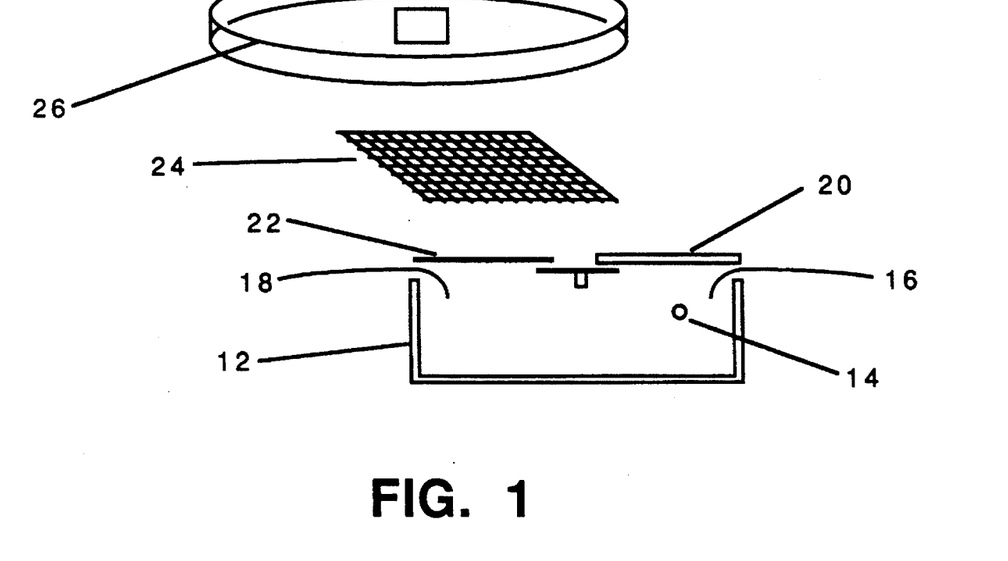
FIG. 1 is an exploded schematic view of the preferred embodiment of a particle accelerator constructed to perform the method of the present invention.
Figure 2:
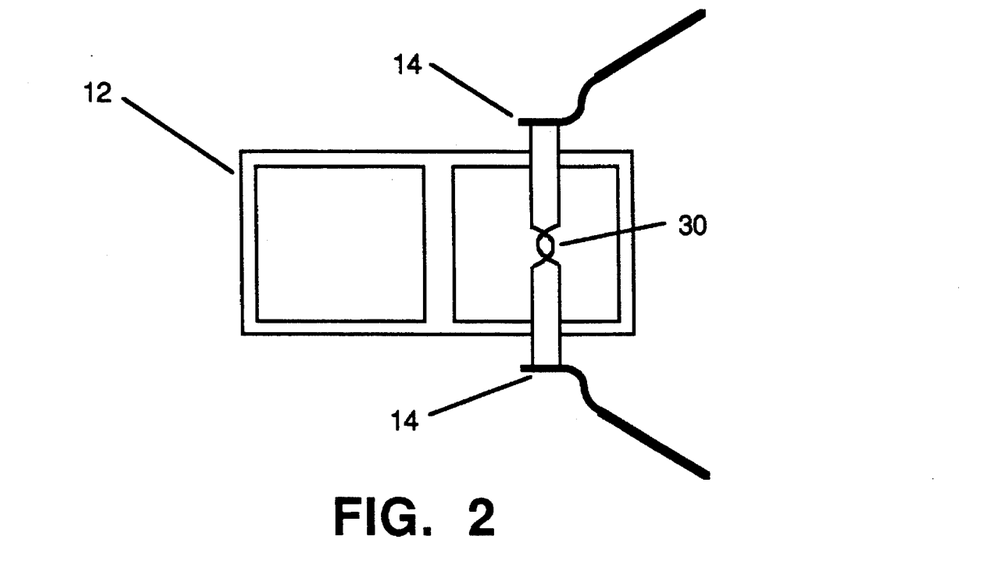
FIG. 2 is a horizontal cross sectional view of the particle accelerator of FIG. 1.

The present invention makes particular use of an apparatus for using an adjustable electric discharge to physically accelerate nucleic acid coated onto small particles into the genetic material of unattached cells. A suitable apparatus for use within the present invention is illustrated in FIGS. 1 and 2. The apparatus consists of a spark discharge chamber 12 into which are inserted two electrodes 14 which are spaced apart by a distance of approximately 1–2 mm. The spark discharge chamber is a horizontally extended rectangle having two openings 16 and 18 out its upward end. One opening 16 is covered by an access plate 20. The other opening, located opposite from the electrodes 14 is intended to be covered by a carrier sheet 22.

The electrodes 14 are connected to a suitable adjustable source of electric discharge voltage. Such a source of electric discharge voltage would preferably include suitable electric switching connected to a capacitor of the 1 to 2 microfarad size range. Preferably, the voltage of the charge introduced into the capacitor is adjustable, such as through the use of an autotransformer, through a range of 1 to 50,000 volts. Suitable switching is provided so that the capacitor can be discharged through the electrodes 14 safely and conveniently by a user.

The carrier sheet 22 intended to be placed upon the opening 18 on the spark discharge chamber 12 is preferably a sheet of aluminized Saran-coated mylar. The carrier sheet 22 should be planar and relatively light. A retaining screen 24 is placed approximately 5–10 millimeters above the opening in the discharge chamber. A target surface 26 is placed approximately 5–25 millimeters above the retaining screen 24.

The nucleic acid construct intended to be transformed into the unattached cells is prepared by suitable DNA preparation techniques well known to one of ordinary skill in the art. The construct is coated onto small particles of a durable, dense, biologically inert material such as gold, the particles typically being 0.2 to 3 microns in size. One source of particularly suitable gold particles is Elicit Industries, Inc. (New York, N.Y.). Preferably, particles are 0.8–1.2 microns.

A PEG (polyethylene glycol) precipitation method is one method used to coat the DNA onto the particles, although other methods would also be suitable. In one tube, 10 mg gold particles, 25 mg DNA and $H_2O$ are mixed to a total volume of 100 µl. 100 µl of 50% PEG 4000 in $H_2O$, 100 µl 1M $CaCl_2$ and 200 µl $H_2O$ are mixed in a second tube. The contents of the first tube are added to the second tube with rapid mixing. The nucleic acid-coated gold particles settle out, and the supernatant is removed.

Alternatively, particles of microcrystalline gold are placed into a tared microfuge tube and weighed. Typically, approximately 10 mg of gold particles are coated at a time. Five volumes (µl/mg) of 0.1M spermadine are added to the gold. Plasmid DNA is added to the mixture to give 0.5–25 µg of DNA per mg of gold particles. The concentration of the plasmid DNA solution is sufficient that the volume of DNA solution added is less than or equal to 0.4 of the volume of spermadine used. The spearmint, DNA and gold are mixed and allowed to incubate at room temperature for 10–15 minutes. Five volumes (µl/mg based on the initial mass of gold used) of 2.5M $CaCl_2$ is added dropwise with constant mixing. The mixture is incubated for 3 minutes at room temperature, then centrifuged for 10–15 seconds to collect the coated particles. Following centrifugation, the supernatant is removed and discarded.

After the particles are coated, they are washed with 100% ethanol and resuspended to the desired "particle loading rate" in 100% ethanol. "Particle loading rate" describes the amount of coated carrier particles placed on the carrier sheet 22. Preferable particle loading rates are 0.05 to 0.5 mg coated particles per $cm^2$ carrier sheet. The coated carrier particles are then placed upon the carrier sheet 22 which is inserted on top of the spark discharge chamber 12. The coated particles are placed on the planar carrier sheet so as to have an even horizontal distribution. This even distribution is important for successful transformation of large numbers of small cells in a statistically significant way. Preferably, an ethanol suspension of coated particles is pipette onto the carrier sheet 22. The coated particles are allowed to settle and most of the ethanol is drained. The residual ethanol is allowed to evaporate, thus leaving a thin, even layer of coated particles.

Unattached mammalian cells are placed on the target surface 26. Suitable cells may come from a cell culture line, or be directly isolated from a mammalian body, as illustrated by the examples below. These cells must be in a liquid suspension. In the examples below, the cells are suspended in culture medium.

It is pivotal to the success of the method of the present invention that the amount of moisture on the target surface 26 be controlled. We have found that efficient transformation is achieved only when the cell/liquid ratio is within certain parameters. In our Examples, we have demonstrated two ways to efficiently control this moisture. One method involves plating cells on a porous surface. Examples of suitable porous surfaces are filter paper (Whatman No. 1, Whatman Paper, Ltd.) and polycarbonate membranes (2–5 µm pore size, Poretics Corp., Livermore, Calif.) Other porous materials may be suitable, but the material must be compatible with cell viability. By "porous" we mean material that will allow excess media to drain away from the target cells, but will retain the cells and allow enough media to remain on the surface of the material to keep the target cells moist and viable. Another method of controlling moisture involves placing an aliquot of the cell suspension (approximately 10–25 µl, containing 1–5 million unattached cells) on the target surface 26 and spreading this liquid into a thin film such that the cell/liquid ratio is suitable for efficient particle bombardment.

A small droplet of water, approximately 2–4 microliters in volume, is placed bridging between the ends of the electrodes 14. The access plate cover 20 is then placed over the top of the discharge chamber 12. Preferably, the atmosphere between the carrier sheet 22 and the target 26 is largely replaced with helium by enclosing the apparatus and target and introducing helium in the enclosure in sufficient quantity to largely displace the atmospheric gases.

Since the carrier sheet 22 is light and rapidly accelerated, it is very flexible. Accordingly, the method propelling the carrier sheet 22 becomes important because a single point force would distort the sheet and not achieve the desired result of a uniform layer of particles travelling into the cells on the target surface 26. A gaseous shock wave is the means employed to impact the carrier sheet 22 and lift it in a planar movement in which the carrier sheet 22 travels across the distance to the retaining screen 24 without losing its shape. The apparatus of FIGS. 1 and 2 achieves this effect through the use of an electric spark discharge. However, there are other means to achieve a similar gaseous shock wave.

At this point a spark discharge between the electrodes 14 is initiated by the use of appropriate electronic switching. The force of the electric discharge bridges the spark discharge gap between the electrodes 14 and instantly vaporizes the small droplet of water placed between the electrodes. The force of the vaporization of that water creates a shock wave within the spark discharge chamber 12 which radiates outward in all directions. The shock wave propels the carrier sheet 22 upwards with great velocity until the carrier sheet 22 contacts the retaining screen 24. The presence of the helium provides less drag on the flight of the carrier sheet and carrier particles as well as less viscous medium to lessen propagation of the shock wave to the target 26.

The carrier sheet 22 is retained at the retaining screen 24, and the coated particles fly off of the carrier sheet and travel freely on toward the target surface. The particles proceed into the target surface and enter the cells. The momentum of the particles as they impact the surface of the target cells is adjustable based on the voltage of the initial electric discharge applied to the electrodes 14. By variations in the amount of the electric energy discharged through the electrodes 14 the velocity by which the particles impact the target can be adjusted. Thus, the depth of penetration of the particles into the cells of a target can be continuously adjusted over the range of adjustment of the electric discharge. Penetration of the particles can also be adjusted by altering the particle size (larger particles usually penetrate further) and shape (spear-shaped particles penetrate further than spherical particles).

After bombardment with the nucleic acid-coated particles, the cells are cultured in appropriate media. The cells are assayed to verify the presence and/or expression of the nucleic acid construct. Suitable assays are disclosed in the examples below. Easily assayed genes, such as disclosed in the examples, may be coupled in tandem with a gene of therapeutic interest. Alternatively, a selection agent, such as an antibiotic resistance gene, could be transformed in tandem with a gene of therapeutic interest. Upon culture with the antibiotic, resistant cells would continue to grow while nonresistant cells would die. Ultimately, these transformed blood cells and blood-cell-progenitor cells would be infused into a patient by procedures known in the art.

Although the unattached cells of some of the examples below seem to be only transiently transformed, the method of the present invention can also result in stable transformation of these cells as shown in another example below. Yang, et al., *Proc. Natl. Acad. Sci.*, USA 87: 9568 (1990) demonstrated that two cell lines were stably transformed at a rate of $2\times10^{-3}$–$6\times10^{-4}$ when subjected to particle bombardment. Additionally, when a variety of plant and bacterial cells were subjected to particle-mediated transformation methods, 0.1%–5% of the transiently expressing transformants proved to be stable transformants. Detection of these stable transformants required screening a large number of transient transformants. Similarly, stable transformation of unattached cells have been detected when statistically large samples of transformed cells are examined. Populations of cells, some of which are stably transformed, can be selected so that the transformed cells can be selectively propagated. This process can lead to a stable population or culture of stably expressing cells which can be returned to the host mammal's body for therapeutic value. Thus, cells can be removed, transformed with a gene for a therapeutic protein (and a selectable marker), selected and proliferated, and then returned to the body to deliver the therapeutic protein.

EXAMPLES

A. TRANSFORMATION OF LYMPHOCYTES

1. Preparation of Lymphocytes

B-cells and T-cells are the two major classes of lymphocytes. In order to investigate the applicability of the present invention to all lymphocytes, we chose to transform cells representative of each type. We chose mouse CTTL-2 cells (ATCC TIB214), which are cytotoxic T-lymphocyte cells and human WIL2-NS cells (ATCC LRL8155), which are B-lymphoblast cells. (Lymphoblasts are immature lymphocytes.) These cells were obtained from ATCC (American Type Culture Collection) and grown in culture medium suggested by the supplier in "Catalogue of Cell Lines and Hybridomas," 6th Ed., 1988, ATCC.

2. Preparation of Nucleic Acid Constructs

Figure 3:
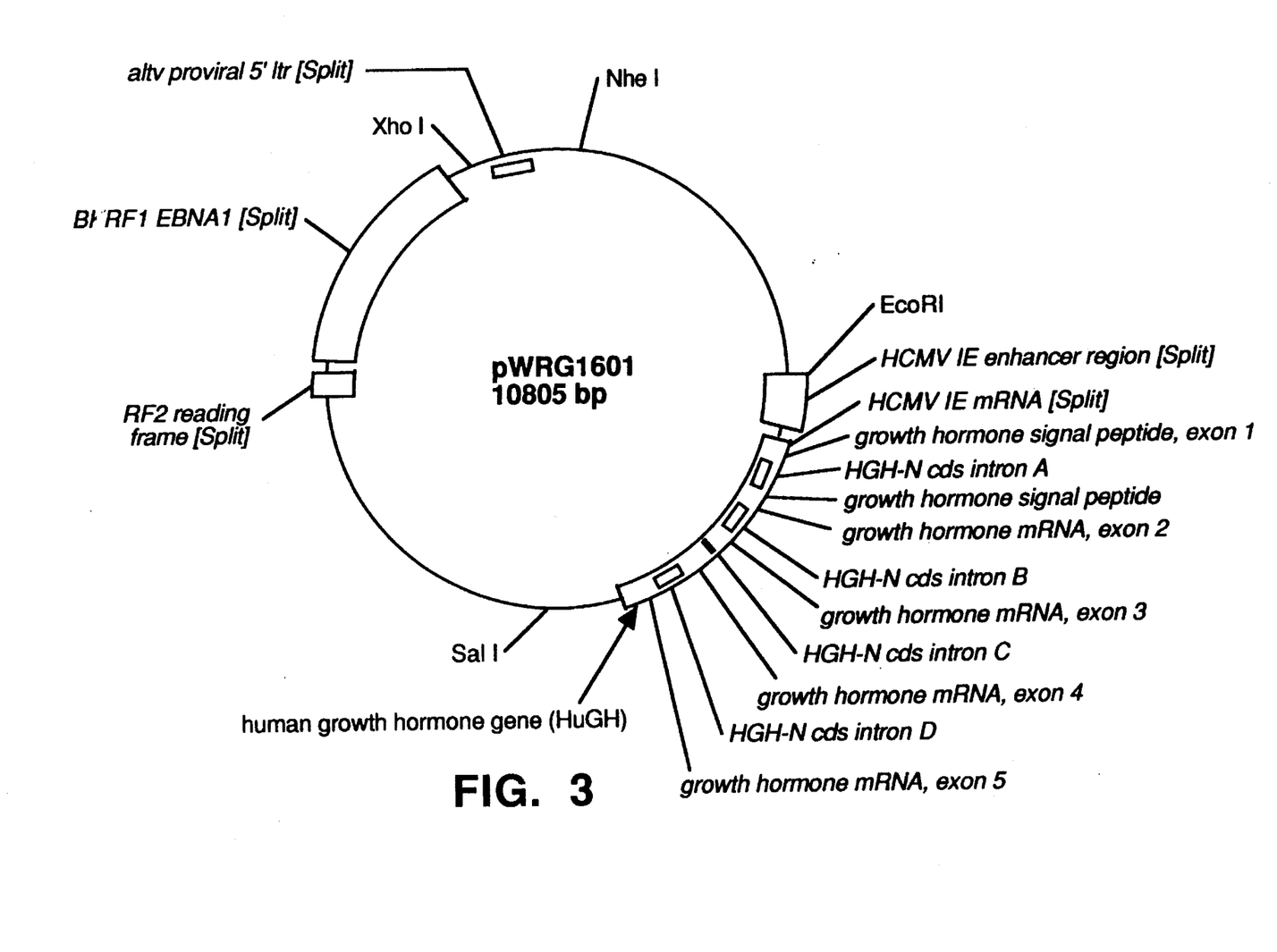
FIG. 3 is a diagram of plasmid pWRG1601.

The lymphocyte cells were transformed with plasmid pWRG1601. FIG. 3 is a diagram of pWRG1601. Transformation with pWRG1601 leads to expression and secretion of human growth hormone in a wide range of mammalian cell types. Plasmid pWRG1601 includes a chimeric gene comprising the human cytomegalovirus (CMV) immediate-early promoter (M. Poser et al. (1985) *Cell* 41: 521–530) and the transcribed region and downstream flanking region from the human growth hormone (HUGH) gene (R. F. Shelden et al. (1986) *Mol. Cell. Biol.* 6: 3173–3179). In addition to the CMV-HuGH gene, pWRG1601 contains regions from Epstein-Barr virus (EBV) that include an origin of replication (ORI P) and a chimeric nuclear antigen 1 (EBNA1) gene, and the bacterial plasmid vector pGEM3 (Promega). The EBV regions provide functions sufficient for autonomous plasmid replication in human and some other mammalian cells, but not in mouse cells. Thus, these regions are nonessential to the present experiments. The pGEM3 regions provide for replication and selection of the plasmid in *E. coli*.

Plasmids were propagated in standard *E. coli* host strains, and plasmid DNA was isolated via conventional methods. Plasmid DNA was coated onto microcrystalline gold particles of 0.8–1.2 microns as described above. The gold particles were coated at 0.5–25 μg of DNA per mg gold particles.

3. Target Preparation

An aliquot of cells in culture medium was counted on a hemocytometer. The cells were then harvested from culture by centrifugation (300×g for 7 minutes) and resuspended in fresh culture medium. An aliquot containing $10^6$–$10^7$ cells was then pipetted onto either a sterile filter paper (Whatmann No. 1) or polycarbonate membrane overlying a sterile filter paper that was prewet with culture medium. The excess culture medium was wicked away by the filter paper.

The target was then bombarded at 10 kV with 163 μg of gold particles coated with pWRG1601. Immediately after blasting, culture medium was added to the target. The cells and medium were then removed and cultured under standard suspension culture conditions as described in the ATCC catalogue (above).

4. Production and Secretion of HuGH by Transformed Lymphocytes

Culture medium from bombarded cells and nonbombarded cells (controls) was analyzed for human growth hormone using a commercial immunoassay kit (Nichols Institute Diagnostics, San Juan Capistrano, Calif.) that specifically detects human growth hormone. At three and seven days after bombardment, lymphocytes were harvested as described above and resuspended in fresh medium. The spent medium was then assayed for HUGH. The medium from nonbombarded cells was used as a control sample to establish background levels for the growth hormone assays.

In all cases, a background level was determined and was essentially the same as the level of samples in which HuGH was not present. Expression and secretion of human growth hormone was detected in both the B-lymphoblasts and the T-lymphocytes that had been subjected to bombardment with particles coated with pWRG1601. By "expression and secretion" we mean that greater than 5 ng of HuGH per $10^6$ cells per day was measured. Transformed B-lymphoblast cultures that expressed and secreted human growth hormone during the culture period were identified for subsequent infusion into mice.

5. Infusion of Mice with Transformed Cells

These experiments have been successfully performed with B-lymphoblasts. Eight days after bombardment, three groups of cells—one control group (nonbombarded WIL2-NS cells) and two groups of WIL2-NS cells transformed with pWRG1601—were counted and divided into aliquots containing approximately $3\times10^6$ cells each. The two groups of bombarded cells were called UF10B and F12A.

The cells were collected from the culture medium by centrifugation at 300×g for 7 minutes. The supernatant medium was removed by aspiration and retained for human growth hormone assay. The cells were resuspended in fresh medium at approximately $10^7$–$10^8$ cells/ml. The growth hormone assays indicate the transformed lymphoblasts were secreting human growth hormone at rates of 10–20 ng/$10^6$ cells/24 hrs. In all cases control cultures showed no production of human growth hormone.

The lymphoblast suspensions (both control groups and transformed groups) were injected into BALB/c mice intravenously, intraperitoneally or subcutaneously. 50 microliters were injected intravenously in the tail vein, 100 microliters were injected intraperitoneally, and 100 microliters were injected subcutaneously and intradermally. Blood samples were collected from the mice two hours after injection of the lymphoblasts. The mice were sacrificed 24 hours after injection, and a final blood sample collected. Analysis of human growth hormone levels in the blood serum gave the results shown below.

TABLE 1

| Route of Injection | Sample | Time post-injection | Serum HuGH (ng/ml)[1] |
|---|---|---|---|
| subQ | UF10B | 2 hr | 88.6 ± 76*[2] |
| subQ | F12A | 2 hr | 0.1 ± 0.4* |
| IP | UF10B | 2 hr | 5.0 ± 0.2 |
| IP | F12A | 2 hr | 4.8 ± 0.6 |
| IV | UF10B | 2 hr | 5.1 ± 3.6 |
| subQ | UF10B | 24 hr | <0.1 ± 0.05* |
| IP | UF10B | 24 hr | 0* |
| IP | F12A | 24 hr | <0.2 ± 0.02* |
| IV | UF10B | 24 hr | <0.1 ± 0.01* |

*These values are not significant.
[1] Average value of two assays ± standard deviation.
[2] One of the assays indicated a high HuGH level while the other did not, resulting in a high standard deviation.

The results show that both intravenous and intraperitoneal injection of transfected lymphoblasts expressing the human growth hormone gene resulted in transient appearance of human growth hormone in circulating blood. One assay from subcutaneous injection gave a significant HuGH reading, but the duplicate assay indicated essentially background levels.

B. TRANSFORMATION OF BONE MARROW CELLS

1. In General

The general protocol of our bone marrow transformation was as follows: Bone marrow cells were flushed from the tibias and femurs of a male Holtzman's rat (approximately 5 weeks old). Bone marrow cell isolation is described in Mishell and Shiigi, *Selected Methods in Cellular Immunology*, p. 11, publ. Freeman and Co., N.Y., 1980. In brief, the rat is first killed and dipped in alcohol. The tibia and femur were separated from the skin and muscle and transferred to a buffer-containing culture dish. The bones were punctured at both ends with a needle and the marrow was expelled by pushing buffer through the bone. The marrow is drawn in and out of the needle to obtain a single-cell suspension.

The bone marrow cells were purified away from red blood cells by centrifugation on Ficoll-Hypaque. Mishell and Shiigi (above, page 205), describe this method. In brief, the method depends on cells of a certain density passing through dense medium and forming a pellet during centrifugation. The pellet contains red blood cells, dead cells, and cell debris. The interface and the Ficoll-Hypaque contain the other cells. The method is as follows: 12 parts of a 14% Ficoll solution are mixed with 5 parts of a 32.8% Hypaque solution and sterilized. The mixture should have a density of 1.09 grams per cm$^3$. The chilled cell solution is prewarmed to 20° C. and layered on top of a 4 ml Ficoll-Hypaque solution in a centrifuge tube. The tubes are placed in a prewarmed centrifuge and centrifuged at 2000×g for 20 minutes. The partially purified bone marrow cells were purified away from the Ficoll-Hypaque by rinsing three times in Hank's basal medium and resuspended in a small volume of culture medium.

Alternatively, red blood cells were partially removed by lysis via hypotonic shock in Example B-1. Red blood cell lysis is described in Mishell and Shiigi (above, p. 22). This procedure is as follows: 0.1 ml of packed cells are diluted with 0.1 ml of diluent (Hank's basal medium) and the cell pellet is resuspended. 1–2 ml of 1/10×diluent is added and mixed into the cells. Cells are exposed for 15 seconds of hypotonic shock, and full strength (1×) diluent is added and mixed. The cell mixture is centrifuged at 200×g for 10 minutes.

The bone marrow cells, purified by either method, were spread in an 18×18 mm pattern on the surface of a 35 mm cell culture dish. This spreading is done by pipetting 10 μl–25 μl of cell suspension onto the center of a 35 mm petri dish and spreading the liquid into a 18×18 mm square with a disposable cell scraper (Baxter McGaw Park, Ill.). We preferably placed 5×10$^6$ cells in 10 μl of medium on each target. We have used 1×10$^6$–5×10$^7$ cells in volumes of 5–50 μl per target with 10 μl being the optimum volume.

Figure 4:
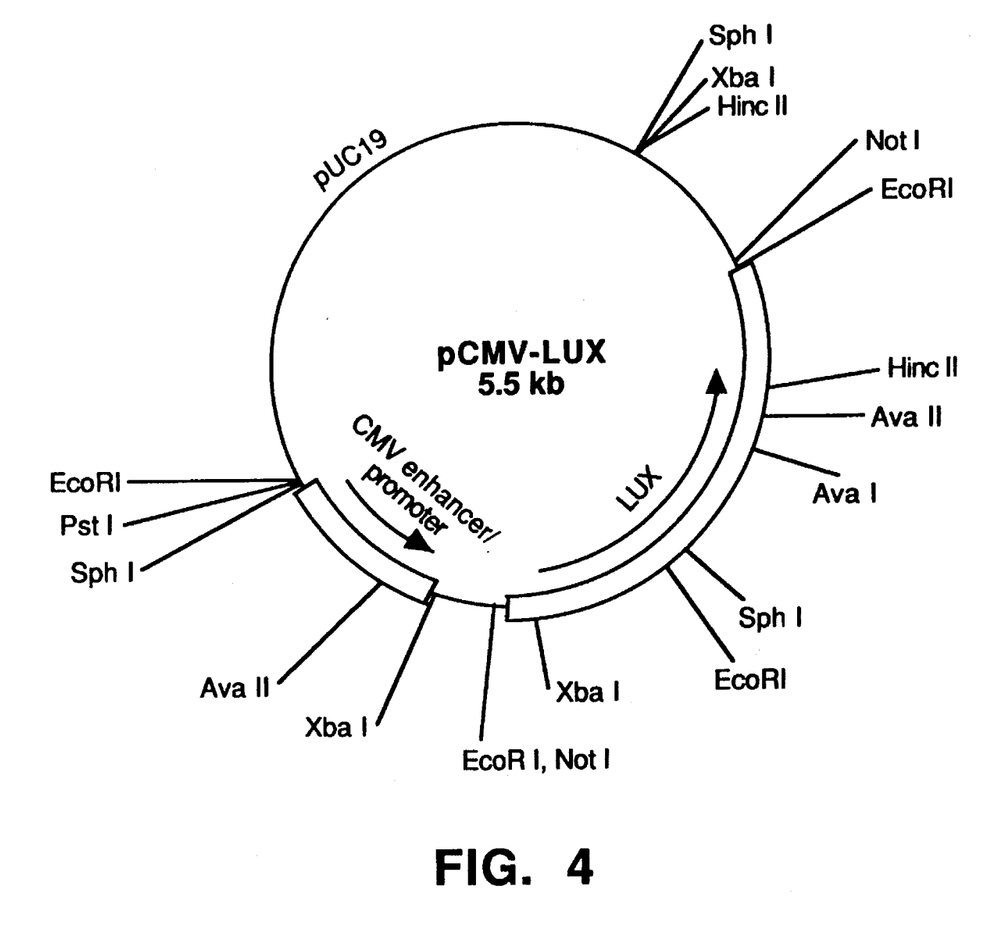
FIG. 4 is a diagram of plasmid CMV-LUX.
Figure 5:
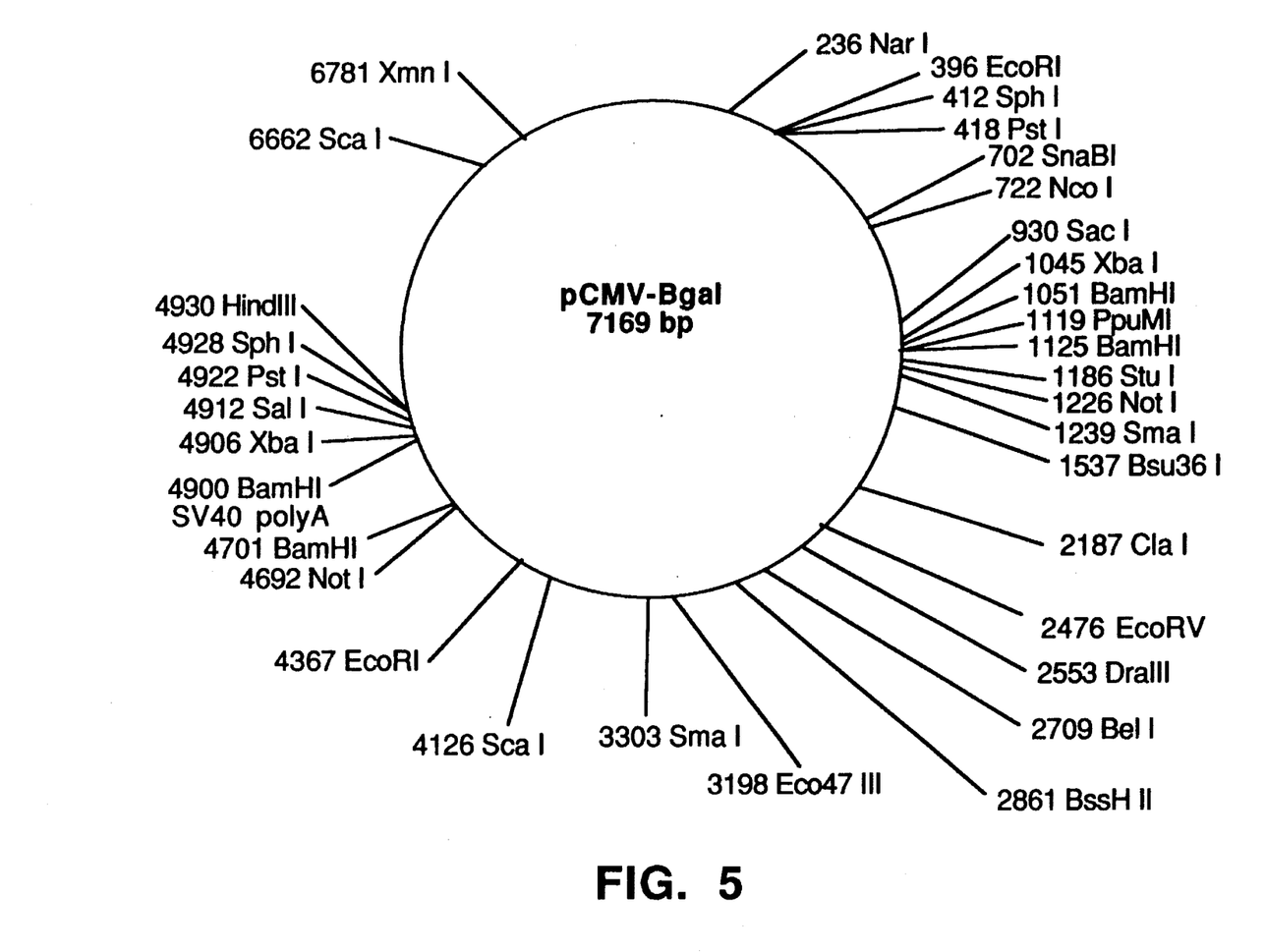
FIG. 5 is a diagram of plasmid CMV-Bgal.
Figure 6:
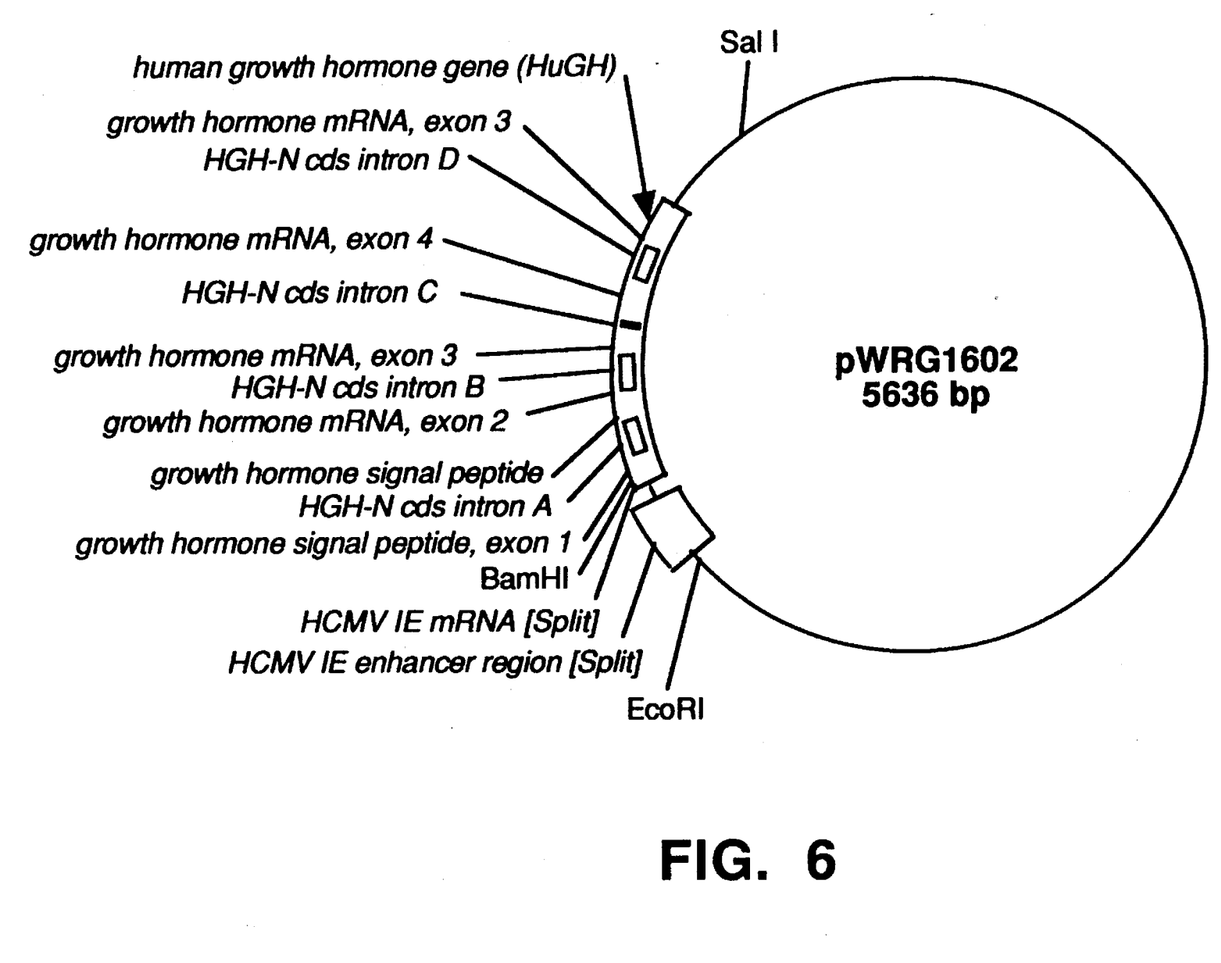
FIG. 6 is a diagram of plasmid pWRG1602.

To coat the particles, plasmid DNA was prepared via standard methods. We chose to bombard the bone marrow cells with the plasmids pCMV-LUX (FIG. 4) and pCMV-Bgal (FIG. 5). The pCMV-LUX plasmid encodes firefly luciferase; the pCMV-Bgal plasmid encodes *E. coli* B-galactosidase.

The cells were bombarded with DNA-coated particles at a voltage of 5–19 kV. Example B-4 demonstrated that the optimum bombardment voltage was 6 kV. After bombardment, 1–2 ml of culture medium was added and the bone marrow cells were cultured overnight by incubation in a 5% $CO_2$: 95% air atmosphere at 37° C. The next day, the cells were assayed for the expression of reporter genes, luciferase and B-galactosidase.

The assay for luciferase was performed as described in deWet, et al., *Mol. Cell. Biol.* 7: 725–737 (1987). In general, the assay measures the oxidation of luciferin, catalyzed by luciferase. The oxidized luciferin emits a photon that we measured using a luminometer (A.L.L. Monolight 2001). The rate of photon production, hence light intensity, provides a measure of luciferase concentration. Extraction buffer (100 mM $KPO_4$, pH 7.5, 100 μg/ml bovine serum albumin, 0.62 mg/ml leupeptin, 2.5 mM phenylmethylsulfonyl fluoride, 1% Triton X-100, 1 mM dithiothreitol) was added to the cells at equal weight:volume. Extraction was performed by triton lysis and sonication. The samples were spun in a refrigerated centrifuge to remove cell debris and the cell-free extract was assayed immediately. In a reaction cuvette, 80 μl of 5×reaction buffer was mixed with distilled water, and 1–50 μl samples of the cell free extracts were added (total volume should equal 400 μl). The mixture was vortexed and 100 μl of 0.5 mM luciferin was added. The amount of luciferase activity was expressed as relative light units (RLU) per bombarded target. 5×reaction buffer is 70 mM glycylglycine, 70 mM magnesium chloride and 50 mg/ml bovine serum albumin, pH adjusted to 7.8.

The assay for B-galactosidase depends on the conversion of 4-methyl-umbelliferyl-beta-D-galactoside (MUG), a nonfluorescent galactoside, to D-galactose and the highly fluorescent methylumbelliferone. The fluorescent product was measured using a fluorometer (excitation set at 350 nm and fluorescence emission read at 450 nm). This assay is extremely sensitive and only a few thousand cells are required for accurate determination of B-galactosidase activity.

The B-galactosidase assay is described in detail in McGregor, et al. *Som. Cell Molec. Genet.*, 13; 253–265 (1987). In brief, cells were resuspended in Z-buffer (60 mM $Na_2PO_4.7H_2O$; 40 mM $NaH_2PO_4.H_2O$; 10 mM KCl; 1 mM $MgSO_4.7 H_2O$, pH to 7.0 with NaOH or HCl.). Up to 105 µl of the cell suspension was deposited on the well of a microtiter dish. 15 µl of 1% Triton X-100 was added to each well. The sample was incubated for 5–10 minutes to solubilize the cells. 30 µl of 3 mM MUG was added to each well. A stop solution (300 mM glycine, 50 mM EDTA, pH 11.2) was added to each well after 90 minutes. The resulting solution was placed in a fluorometer and the fluorescence intensity was measured.

2. Transformation of Bone Marrow: Luciferase

Bone marrow cells from two rats were harvested as in our standard protocol and pooled. In this Example, we compared two ways of partially purifying the bone marrow. We wanted to remove the red blood cells, but wanted to leave the marrow cell population as crude as possible beyond that. Most workers use Ficoll-Hypaque (F/H) purified cells. However, some bone marrow cells are lost to the pellet during centrifugation in this method. We tried lysis of red blood cells by hypotonic shock as an alternative. Hypotonic shock was performed as described above.

The purified bone marrow cells were concentrated by centrifugation (300×g, 5 minutes) resuspended in a small volume of medium, and spread onto target surfaces as described above. The "hypotonic shocked" cells were concentrated to $6 \times 10^6$ cells/10 µl. The ficoll/hypaque-purified cells were concentrated to $2.6 \times 10^6$ cells/10 µl. 10 µl of each sample was spread on the target surface. The cells were then bombarded at 10 kV with pCMV-LUX and culture medium was immediately added. The results of this experiment, Table 2, indicated similar transformation frequency for either method of partial purification of the bone marrow cells.

TABLE 2

| Sample # | Particle Loading Rate | Isolation | Results |
| --- | --- | --- | --- |
| 5 | 0.2 mg/cm² | F/H | 12884 RLU/target |
| 6 | 0.2 mg/cm² | Hypotonic shock | 46232 RLU/target |
| 7 | 0.4 mg/cm² | F/H | 21632 RLU/target |
| 8 | 0.4 mg/cm² | Hypotonic shock | 40790 RLU/target |

3. Transformation of Bone Marrow

In this Example, we tested different cell concentrations on the target surface to find which concentration gave the highest transient activity without wasting cells. The cells were bombarded at 10 kV, 0.3 mg/cm² particle loading rate on the carrier sheet, using pCMV-Bgal. We plated 10 µl of cell suspension onto the target surface. Table 3 tabulates the results, which show that a certain cell density is required for optimal gene transfer.

TABLE 3

| Sample # | Cells per target | Relative MUG Activity/ 10⁶ cells |
| --- | --- | --- |
| 1 | 2.5 × 10⁶ | 1 |
| 2,3 | 5 × 10⁶ | 4.5 |
| 4,5 | 7.5 × 10² | 4.75 |
| 6,7 | 1 × 10⁷ | 6.75 |
| 8,9 | 2.5 × 10⁷ | 3.5 |

The values obtained with the MUG fluorometric assay have been normalized to the $1 \times 10_6$ cell level. The results indicate that $1 \times 10^7$ cells per 10 µl per target was the most efficient use of cells.

4. Transformation of Bone Marrow: Agglutinin Treatment

Cells in this Example were extracted as per our protocol. We used a soybean agglutinin (SBA) treatment to fractionate the bone marrow cells into two populations based on ability of the cells to be agglutinated by SBA, a lectin that binds specific residues on the surface of more mature lymphoid cells. Undifferentiated bone marrow stem cells should not bind SBA.

Soybean agglutinin treatment is as described in Mishell and Shiigi (above, page 226). In brief, cells are mixed with an equal volume of SBA-containing solution and incubated for 5–10 minutes at room temperature. The cells are layered on top of 40 ml of buffer containing 2% bovine serum albumin and incubated at room temperature for 15–30 minutes allowing separation of agglutinated and non-agglutinated cells. The top and bottom layers of cells were removed separately and transferred to centrifuge tubes with Pasteur pipettes. The bottom layer of cells was suspended in 0.2M galactose and incubated at room temperature. The cells were pelleted and washed twice with the galactose solution and once with buffer before using.

Before bombarding, the cells in the SBA+ #2 sample were placed on a 5 µm polycarbonate membrane placed in a petri dish.

Results shown in Table 4, indicate luciferase expression in both samples.

TABLE 4

| Sample | Support | Results |
| --- | --- | --- |
| SBA+ #2 | 5 µM polycarbonate | 91817 RLU/target |
| SBA+ #4 | plastic culture dish | 88610 RLU/target |

5. Transformation of Bone Marrow: Power Study

This Example was a calibration of the kV charge used to bombard the cells. We found that 6 kV is the optimum kV for the bone marrow cells using the other parameters we had developed ($1 \times 10^7$ cells/10 µl/target, Particle loading rate= 0.1 mg/cm²). Table 5 shows these results.

TABLE 5

| Sample | kV | Results |
| --- | --- | --- |
| 1,2 | 6 | 34969 RLU/target |
| 3,4 | 8 | 13027 RLU/target |
| 5,6 | 10 | 740 RLU/target |

6. Bone Marrow: Human Growth Hormone

In this example, we investigated SBA agglutination treatment and transformation with a plasmid encoding the human growth hormone (HUGH) gene, pWRG1602. Extraction and concentration of the bone marrow cells were as per the standard protocol. The cells were bombarded with plasmids pCMV-LUX and pWRG1602. We assayed for the presence of HuGH with a commercial immunoassay kit (Nichols).

The results, Table 6, showed that the SBA agglutination increased transient activity approximately two-fold. Although SBA is a lectin, it has not been reported to be a mitogen for human or murine lymphocytes. The original purpose of the SBA treatment was to partially purify progenitor cells, not stimulate transient activity.

TABLE 6

| Treatment (24 Hrs) | HuGH CPM (24 Hrs) | HuGH (CPM) (72 Hrs) | Lux(RLU/target) (24 Hrs) |
| --- | --- | --- | --- |
| NONE | 2427 | 2035 | 128028 |
| SBA | 5723 | 4390 | 228615 |

7. Bone Marrow: Fetal Calf Serum

This experiment tested different resuspension media and concentrations of fetal bovine serum (FBS). AIM-V and RPMI are standard mammalia culture media distributed by Gibco, Co. The RPMI medium without FBS gave the highest LUX counts we had ever recorded, even though cell counting showed that fewer viable cells were present at the time of assay. For this experiment we calculated the amount of luciferase protein to total extractable protein.

TABLE 7

| Medium After Blast | LUX RLU/ Target | pg LUX/ mg total protein |
| --- | --- | --- |
| AIM-V | 240777 | 85 |
| RPMI | 642928 | 234 |
| RPMI + 10% FBS | 379550 | 77 |
| RPMI + 20% FBS | 277316 | 48 |

C. STABLE TRANSFORMATION AND SELECTION

This example was performed with CTTL-2 cells, which are mouse T-lymphocytes. The CTTL-2 cells were collected and transformed using the membrane target assembly procedure described above. Approximately $5 \times 10^7$ CTTL-2 cells were transformed by particle acceleration powered by 9.5 kV, at 18 mm of helium, with a particle loading rate of 0.05 mg per cm$^2$ of carrier sheet. The DNA used was pWRG 1601 (at 1 µg/mg particles) and pRSV-neo (at 0.5 µg/mg particles). The particles were all coated with a mixture of the plasmids. The plasmid pRSV-neo includes a mammalian cell expression cassette for resistance to geneticin. After particle bombardment, the cells were returned to culture for two days, after which the cells were diluted 1:10 with fresh medium containing 0.3 mg/ml geneticin, and then were divided into eight equal aliquots in tissue culture flasks (T75). The geneticin was intended to select for cells expressing the RSV-neo gene construct.

After 18 days in culture under selection, the cells were washed to remove any growth hormone that might have accumulated in the medium. The cells were resuspended in fresh medium with 0.3 mg/ml geneticin and cultured for 24 more hours. At this time, the medium was collected and assayed for the presence of human growth hormone secreted by the cells. The results of this assay are presented in Table 8 below.

TABLE 8

| Flask No. | 1 | 2 | 3 | 4 | 5 | 6 | 7 | 8 |
| --- | --- | --- | --- | --- | --- | --- | --- | --- |
| HuGH (ng/ml) | 2.0 | 1.9 | 1.4 | 1.2 | 1.3 | 1.8 | 1.4 | 2.2 |

The cells were again diluted 1:10 in fresh medium, this time with 0.6 mg/ml geneticin and each culture was split into four aliquots. The aliquots were cultured for six more days (26 days after transformation) and then were again subcultured as above and the medium collected for analysis. This time, the cultures were permitted to accumulate hormone for 72 hours. The results are summarized in the following Table 9.

TABLE 9

| Culture | Subculture | HuGH(ng/ml) |
| --- | --- | --- |
| 1 | A.1 | 49.6 |
|   | A.2 | 51.2 |
|   | B.1 | 59.2 |
|   | B.2 | 64.0 |
| 2 | A.1 | 49.6 |
|   | A.2 | 44.8 |
|   | B.1 | 50.4 |
|   | B.2 | 57.6 |
| 3 | A.1 | 9.6 |
|   | A.2 | 9.6 |
|   | B.1 | 8.8 |
|   | B.2 | 8.0 |
| 4 | A-1 | 3.4 |
|   | A.2 | 3.6 |
|   | B.1 | 3.0 |
|   | B.2 | 3.8 |
| 5 | A.1 | 8.4 |
|   | A.2 | 5.3 |
|   | B.1 | 4.5 |
|   | B.2 | 5.4 |
| 6 | A.1 | 11.2 |
|   | A.2 | 12.0 |
|   | B.1 | 12.4 |
|   | B.2 | 24.0 |
| 7 | A.1 | 1.8 |
|   | A.2 | 2.2 |
|   | B.1 | 1.2 |
|   | B.2 | 1.8 |
| 8 | A.1 | 39.2 |
|   | A.2 | 24.8 |
|   | B.1 | 35.2 |
|   | B.2 | 44.8 |

The cultures 1.B.1, 1.B.2, 2.B.2, 6.A.1 and 8.B.2 were selected for further propagation. Culture 8.B.2 became contaminated, however, and was discontinued. After an additional eight days of culture (34 days from transformation), the remaining cultures were again diluted into fresh medium with 0.6 mg/ml geneticin and the 48 hour accumulation of HuGH was measured. At this point, significant differences between cultures in the densities of the cells were noted. To compensate for this, the results in the following Table 10, setting for the result of assay for hormone in these cultures, also presents data on the basis of HuGH per one million cells.

TABLE 10

| Culture | ng HuGH/ml | ng HuGH/ml/ 24 hrs | ng HuGH/10$^6$ cells 24 hrs |
| --- | --- | --- | --- |
| 1.B.1.1 | 11.2 | 5.6 | 28.0 |
| 1.B.1.2 | 10.4 | 5.2 | 26.0 |
| 1.B.1.3 | 9.6 | 4.8 | 24.0 |
| 1.B.1.4 | 3.4 | 1.7 | 8.5 |
| 1.B.2.1 | 13.6 | 6.8 | 22.7 |
| 1.B.2.2 | 10.6 | 5.0 | 16.7 |
| 1.B.2.3 | 9.6 | 4.8 | 16.0 |
| 1.B.2.4 | 8.8 | 4.4 | 14.7 |
| 2.B.2.1 | 12.0 | 6.0 | 30.0 |
| 2.B.2.2 | 11.2 | 5.6 | 28.0 |
| 2.B.2.3 | 12.0 | 6.0 | 30.0 |
| 2.B.2.4 | 12.4 | 6.2 | 62.0 |
| 6.A.1.1 | 32.0 | 16.0 | 40.0 |
| 6.A.1.2 | 34.4 | 17.2 | 43.0 |
| 6.A.1.3 | 33.6 | 16.8 | 42.0 |
| 6.A.1.4 | 35.2 | 17.6 | 44.0 |

Cultures 1.B.1.1–4 and 1.B.2.1–4, etc. were pooled and preserved by freezing. Aliquots of the pooled cultures 1.B.1, 1.B.2 and 2.B.2 have also been maintained continuously in culture in selective medium. The pooled cultures were assayed again at 37 and 47 days after transformation. The results were levels of HuGH expression of 14.6 and 13.7 ng of HuGh/ml/24 hours for 37 and 47 days respectively. The cultures remained resistant to geneticin. The time of culture, the continued resistance, and the continued expression of HuGH verified stable transformation. The increase in HuGH levels in propagation also indicates that the cell population was being enriched for cells expressing HUGH. The cultures were, however, not clones and seemed to comprise numerous independent transformed lineages. This heterogeneity accounts for the varied behavior of the different culture aliquots in successive passages.

This data demonstrates the practicality of genetic therapy using such unattached cells. Unattached cells, such as lymphocytes, may be removed from the body, and then may be transformed by particle acceleration, and selected in culture. The selected transformant cells can be proliferated in culture, and returned to the body in appropriate numbers. Long term culture of the selected cells also appears possible. The transformant cells re-introduced in the body would express the introduced gene for whatever therapeutic objective that is desired.

We claim:

1. A method of genetically transforming mammalian unattached cells, comprising the steps of:

(a) preparing copies of a nucleic acid construct which is expressed in mammalian cells;

(b) coating the copies of the nucleic acid construct onto biologically inert carrier particles;

(c) isolating mammalian unattached cells from a liquid suspension and placing them onto a porous support surface selected from the group consisting of paper and a polycarbonate membrane in such a manner that the cells retain sufficient moisture exposure to remain viable, the unattached mammalian cells selected from the group consisting of lymphocytes and bone marrow cells;

(d) accelerating the carrier particles produced in step (b) into the cells such that some of the particles lodge in the interior of at least some of the cells; and (e) verifying the existence and expression of the nucleic acid construct in the treated cells.

2. The method of claim 1 additionally comprising the step of layering the carrier particles produced in step (b) onto a planar carrier sheet.

3. The method of claim 2 wherein the carrier sheet is accelerated by a gaseous shock wave.

4. The method of claim 1 wherein the carrier particles are 0.2–3 micron gold beads.

5. The method of claim 1 wherein the cells are lymphocytes.

6. The method of claim 1 wherein the cells are bone marrow cells.

7. The method of claim 1 wherein the cell suspension of step (c) is approximately $1 \times 10^6$ cells/µl liquid.

8. The method of claim 1 wherein the volume of cell suspension in step (e) is approximately 10 µl.

9. The method of claim 1 further comprising, after step (e), selecting for cells from step (e) which express a selection agent gene included in the nucleic acid construct.

10. The method of claim 9 further comprising, after selecting for cells which express said selection agent gene, the step of culturing the selected cells to create a population of stably transformed and expressing cells.

11. A method of genetically transforming mammalian unattached cells comprising the steps of:

(a) preparing copies of a nucleic acid construct which expresses a gene product in mammalian cells;

(b) coating copies of the nucleic acid construct onto carrier particles of dense material;

(c) layering the carrier particles produced in step (b) on a planar carrier sheet;

(d) placing the carrier sheet onto a spark discharge chamber;

(e) placing a droplet of water between the end of a pair of spaced electrodes within said spark discharge chamber so as to bridge the gap between the electrodes;

(f) isolating mammalian unattached cells from a liquid suspension, the unattached mammalian cells selected from the group consisting of lymphocytes and bone marrow cells;

(g) placing the cells on a porous target surface, selected from the group consisting of filter paper and polycarbonate membrane, wherein the amount of moisture in the target surface is minimal, but sufficient for cell viability;

(h) initiating a discharge of high voltage electric force between the electrodes so that a spark bridges the gap between the electrodes, vaporizing the water droplet and accelerating the carrier sheet toward the cells, the carrier sheet being restrained from hitting the cells but the carrier particles traveling into the cells, the force with which the carrier particles are accelerated into the cells being adjustable by adjusting the voltage of the high voltage electric force applied to the electrodes so that the nucleic acid construct is introduced into the cells with minimal damage to the cells; and (i) verifying the existence and expression of the construct in the cells.

12. The method of claim 11 wherein voltage across the electrodes in step (h) is approximately 7–10 kV.

* * * * *